United States Patent [19]

De Lucchi et al.

[11] Patent Number: 4,713,466

[45] Date of Patent: Dec. 15, 1987

[54] PROCESS FOR THE PREPARATION OF ISOSORBIDE-5-MONONITRATE

[75] Inventors: Ottorino De Lucchi; Fabiola Filippuzzi; Giorgio Modena, all of Padova; Ettore Camera, Gorizia, all of Italy

[73] Assignees: Consiglio Nazionale Delle Richerche, Rome; Dinamite, Udine, both of Italy

[21] Appl. No.: 861,705

[22] Filed: May 12, 1986

[30] Foreign Application Priority Data

May 10, 1985 [IT] Italy ................. 20660 A/85

[51] Int. Cl.$^4$ ............................ C07D 493/04
[52] U.S. Cl. ................................... 549/464
[58] Field of Search ......................... 549/464

[56] References Cited

U.S. PATENT DOCUMENTS 4,381,400  4/1983  Emeury et al. ............. 549/464

Primary Examiner—Henry R. Jiles
Assistant Examiner—Bernard I. Dentz
Attorney, Agent, or Firm—Parkhurst & Oliff

[57] ABSTRACT

A selective process for the preparation of isosorbide-5-mononitrate (I)

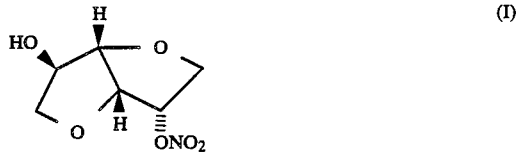

from isosorbide-2,5-dinitrate (II)

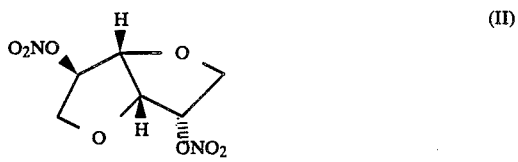

Said preparation is carried out by treating isosorbide-2,5-dinitrate with a suitable reduction system in the presence of not easily oxidizable coordinating metal ions.

10 Claims, No Drawings

PROCESS FOR THE PREPARATION OF ISOSORBIDE-5-MONONITRATE

TECHNICAL FIELD

This invention relates to a new process for the preparation of isosorbide-5-mononitrate (I):

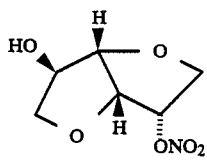

More particularly, the invention relates to a selective process for the preparation of isosorbide-5-mononitrate (I) from isosorbide-2,5-dinitrate (II):

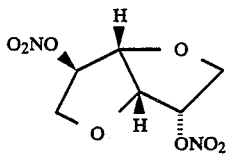

BACKGROUND

Isosorbide-5-mononitrate (I) is a compound which is currently much sought after in the pharmaceutical field because of its therapeutic properties in the treatment of coronary illnesses, in particular in the treatment of angina pectoris.

Isosorbide-2,5-dinitrate (ISDN) is known to exhibit an analogous pharmacological action. However, isosorbide-5-mononitrate has the following advantages (W. Schaumann, Medwelt Bd. 32/Heft 14a 1981; T. Taylor. L. F. Chasseaud, R. Major, E. Doyle and A. Darragh, Biopharm. & Drug Disp., Vol. 2, 255-263, 1981):

(a) In the metabolic process it provides only one mole of nitric acid instead of two.

(b) In contrast to ISDN which metabolises into its two mononitrate isomers, it consists of a single active substance rather than three substances, the concentration ratios and thus the activities of which vary mutually with time.

(c) It undergoes much slower metabolism and therefore exhibits a more lasting action.

(d) It becomes distributed not only within the plasma but also throughout a much wider extent which can be approximated to that of the total body water.

One difficulty which makes the synthesis of isosorbide-5-mononitrate (I) costly is the need to prepare it by a selective method which enables it to be easily separated from its isosorbide-2,5-dinitrate isomer.

Various processes are known in the art for preparing isosorbide-5-mononitrate (I).

For example, a process is known for preparing isosorbide-5-mononitrate (I) by direct nitration of isosorbide (III)

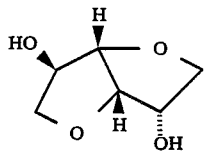

(I. G. Csizmadia, L. D. Hayward, Photochem. Photobiol. 4, 657, 1975; German Pat. No. 2,221,080).

According to a further process, isosorbide-5-mononitrate is prepared by partial basic or acid hydrolysis of isosorbide-2,5-dinitrate (L. D. Hayward et al., Can. J. Chem., 45, 2191, 1967).

These two processes involve dangerous operations because of which they are difficult to apply, and also give low yields.

According to further processes, isosorbide (III) is firstly protected in position 2, for example by acylation, and is then nitrated in position 5, after which the position 2 protector group is removed by hydrolysis (U.S.A. Pat. No. 4,065,488, German Pat. No. 2,951,934 and European Pat. No. 0045076).

According to a modification (European Pat. No. 0057847), the 2-acyl derivative which forms from the other components in the presence of catalysts is distilled from the reaction mixture. A process is also known (German Pat. No. 2,903,927) which leads to the preparation of (I) from isomannide by tosylation, transesterification, nitration and hydrolysis.

A process is also known based on the reduction of isosorbide-2,5-dinitrate, in which hydrazine hydrate is used as the reagent (French Pat. No. 2,103,906).

This however is a non-selective process in that both the monosubstituted isomers form in a ratio which is insufficiently high to allow economically convenient separation. Moreover, hydrazine is a known carcinogen.

All known processes are difficult to apply industrially.

SUMMARY OF THE INVENTION

We have now discovered a process for the preparation of isosorbide-5-mononitrate (I) by which the drawbacks of the known art are obviated, and in particular a process in which:

- the operating conditions are simple and safe;
- low-cost reagents are used;
- high yields and selectivity are obtained;
- industrial application is simple and economically convenient.

The process for the preparation of isosorbide-5-mononitrate (I) from isosorbide-2,5-dinitrate (II) according to the present invention is characterised in that the isosorbide-2,5-dinitrate (II) is treated, in a reaction medium consisting of an organic solvent, with a reduction system in the presence of not easily oxidisable coordinating metal ions, to obtain isosorbide-5-mononitrate (I) with high selectivity.

DETAILED DESCRIPTION OF PREFERRED EMBODIMENTS

These and further characteristics and advantages of the process according to the present invention will be more apparent from the detailed description of preferred embodiments of the present invention given hereinafter by way of illustration.

Various types of reduction system can be used in the process according to the invention.

The reduction system can consist of a metal and a weak acid, said metal forming not easily oxidisable coordinating ions in said weak acid.

In this case the ions for the process are produced in situ.

The metal preferably used is zinc, and the weak acid preferably used is acetic acid.

The reduction system can also consist of hydrogen in the presence of a reduction catalyst such as palladium on carbon.

In this case the not easily oxidisable coordinating metal ions are added in the form of salts.

The reaction medium consists of organic solvents such as ethyl alcohol, acetonitrile, ethyl acetate etc., either containing or not containing water.

If the reduction system consisting of zinc and acetic acid is used, the isosorbide-2,5-dinitrate is dissolved at ambient temperature in an ethyl alcohol mixture either containing or not containing water in a reactor provided with a cooling jacket, and powdered zinc is added to the solution.

The suspension is cooled under agitation to a temperature of between $-30°$ and $0°$ C., the temperature of the system being controlled at this value, and then zinc and a portion of the acetic acid equivalent to 2% of the total volume are added under agitation. After 6–8 hours a further portion of the three components is added, and after a further 6–8 hours acetic acid is gradually added until the reaction is complete.

The suspension is then filtered, concentrated and treated with $CH_2Cl_2$ and then with $H_2O$. The organic phase is separated and dried with $MgSO_4$. The solvent is removed by evaporation, and the isosorbide-5-mononitrate is crystallised by adding a seed crystal of the same product.

The yield of the crude product is between 70 and 85%, and the degree of purity of the crystallised product is 97–98%, with a final yield of 50–60%.

If hydrogen in the presence of palladium on carbon is used as the reduction system, the isosorbide-2,5-dinitrate is dissolved in an ethyl alcohol mixture either containing or not containing water, and a catalytic quantity of palladium on carbon or of another catalyst is then added.

A not easily oxidisable coordinating metal salt is then added, in a molar ratio of between 0.8 and 1.2 with respect to the isosorbide-2,5-dinitrate.

Preferably, said compound is nickel (II) chloride.

The air contained in the reactor is eliminated and replaced by hydrogen, which is maintained for the entire reaction time at a pressure slightly exceeding atmospheric.

The reaction is conducted under agitation at a temperature of between $0°$ and $25°$ C. for a time of between 1 and 12 hours.

Isosorbide-5-mononitrate is obtained with good selectivity.

Any unreacted isosorbide-2,5-dinitrate can be recycled to the next preparation.

The following non-limiting examples are given to illustrate the characteristics of the process according to the invention.

EXAMPLE 1

5 g (21.2 mmoles) of isosorbide-2,5-dinitrate and 3 g of powdered zinc are placed in a 250 ml laboratory flask fitted with a cooling jacket, thermometer and agitator, and containing 100 ml of a mixture of alcohol and water in a volume ratio of 70/30. The mixture is stirred at controlled temperature of $-15°$ C. and 2 ml of glacial acetic acid are added.

After 7 hours, 1 ml of glacial acetic acid, 3 g of powdered zinc, 3 g (12.7 mmoles) of isosorbide-2,5-dinitrate and 25 ml of ethyl alcohol are added.

The mixture is kept under agitation for a further 7 hours at $-15°$ C., after which glacial acetic acid is gradually added until the reaction of the isosorbide-2,5-dinitrate is complete, as ascertained by GLC analysis.

The system is filtered and concentrated to a volume of 30–40 ml to obtain a product mixture having the following composition:

| | |
|---|---|
| isosorbide | 15% |
| isosorbide-2-mononitrate | 2% |
| isosorbide-5-mononitrate | 75% |
| unreacted isosorbide-2,5-dinitrate | 8% |

200 ml of $CH_2Cl_2$ are added and the mixture filtered. 50 ml of water are added and the organic phase is separated and dried with $MgSO_4$. The solvent is evaporated to minimum volume and a seed crystal of isosorbide-5-mononitrate is added to crystallise 3.8 g (19.9 m moles) of product, which is found to be isosorbide-5-mononitrate of 97% purity.

The crude product yield is 77% and the final product yield is 58%.

EXAMPLE 2

A 100 ml laboratory flask is fitted with a two-way cock connected respectively to a vacuum pump and to a rubber balloon containing hydrogen under a pressure slightly exceeding atmospheric. 30 ml of a mixture of ethanol and water in a volume ratio of 70/30, 2 g (8.5 mmoles) of isosorbide-2,5-dinitrate, 10 mg of 10% palladium on carbon, and 2 g (8.5 mmoles) of $NiCl_2$ are fed in.

The mixture is deaerated several times by means of the vacuum pump, replacing the air contained in the flask with hydrogen from the rubber balloon.

The mixture is kept under agitation in a hydrogen atmosphere at ambient temperature for 12 hours.

A product mixture is obtained which, excluding the unreacted isosorbide-2,5-dinitrate, has the following composition:

| | |
|---|---|
| isosorbide | 27% |
| isosorbide-5-nitrate | 61% |
| isosorbide-2-nitrate | 12% |

EXAMPLE 3

(Comparison example)

The experiment of Example 2 is repeated, using the same conditions and same operating method, but without adding the nickel chloride.

At the end of the experiment a product mixture is obtained which, excluding the unreacted isosorbide-2,5-dinitrate, has the following composition:

| | |
|---|---|
| isosorbide | 23% |
| isosorbide-5-nitrate | 47% |

| -continued | |
|---|---|
| isosorbide-2-nitrate | 30% |

Comparing Example 3 with Example 2, the importance of the nickel chloride in orienting the reaction towards the selective production of isosorbide-5-mononitrate can be clearly seen.

We claim:

1. A process for the preparation of isosorbide-5-mononitrate (I)

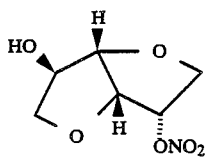

from isosorbide-2,5-dinitrate (II)

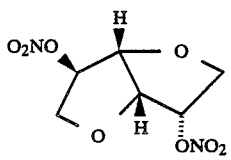

wherein the isosorbide-2,5-dinitrate (II) is treated, in a reaction medium consisting of an organic solvent either containing or not containing water, with a reduction system in the presence of not easily oxidisable coordinating metal ions.

2. A process as claimed in claim 1, wherein said reduction system consists of a metal and a weak acid, said metal forming in said weak acid said not easily oxidisable coordinating metal ions.

3. A process as claimed in claim 2, wherein said metal is zinc and said weak acid is acetic acid.

4. A process as claimed in claim 1, wherein said reduction system consists of hydrogen in the presence of a reduction catalyst and a not easily oxidisable coordinating metal salt.

5. A process as claimed in claim 4, wherein said reduction catalyst consists of palladium on carbon.

6. A process as claimed in claim 4, wherein the not easily oxidisable metal salt is nickel (II) chloride.

7. A process as claimed in claim 1, wherein said metal ions are $Zn^{++}$ or $Ni^{++}$ ions.

8. A process as claimed in claim 3, wherein said treatment of isosorbide-2,5-dinitrate (II) with zinc and acetic acid is carried out at a temperature of between $-30°$ and $0°$ C.

9. A process as claimed in claim 4, wherein said treatment of isosorbide-2,5-dinitrate (II) with a reduction system consisting of hydrogen in the presence of a reduction catalyst is carried out at a temperature of between $0°$ and $25°$ C.

10. A process as claimed in claim 2, wherein said metal is zinc.

* * * * *